United States Patent [19]
Drevillon et al.

[11] Patent Number: 5,666,200
[45] Date of Patent: Sep. 9, 1997

[54] METHOD OF ELLIPSOMETRIC MEASUREMENT, AN ELLIPSOMETER AND DEVICE FOR CONTROLLING THE CARRYING OUT OF LAYERS USING SUCH METHOD AND APPARATUS

[75] Inventors: Bernard Drevillon, Meudon; Morten Kildemo, Palaiseau; Ramdane Benferhat, Oncy Sur Ecole, all of France

[73] Assignee: Instruments S.A., Paris, France

[21] Appl. No.: 607,810

[22] Filed: Feb. 27, 1996

[30] Foreign Application Priority Data

Feb. 27, 1995 [FR] France ................................ 95 02263

[51] Int. Cl.$^6$ ........................................................ G01N 21/21
[52] U.S. Cl. ............................................. 356/368; 356/369
[58] Field of Search ......................................... 356/364, 365, 356/366, 367, 368, 369; 250/225

[56] References Cited

PUBLICATIONS

Drevillon et al, "Design of a new in situ spectroscopic phase modulated ellipsometer" SPIE vol. 1188 Multichamber and In-Situ Processing of Electronic Materials (1989) pp. 174–184 (no month) 1989.

"A Reflectance Anisotropy Spectrometer for Real–Time Measurements," O. Acher et al., Rev. Sci. Instrum., vol. 63, No. 11, Nov. 1992, pp. 5332–5339.

"Virtual Interface Method for In Situ Ellipsometry of Films Grown on Unknown Substrates," F. K. Urban, III et al., Journal of Vacuum Science & Technology, Part A, vol. 11, No. 4, Jul./Aug. 1993, pp. 976–980.

"In Situ Spectral Ellipsometry for Real–Time Thickness Measurement: Etching Multilayer Stacks," Steven A. Henck et al., Journal of Vacuum Science & Technology, Part A, vol. 11, No. 4, Jul./Aug. 1993, pp. 1179–1185.

"In Situ Characterization of Plasma–Deposited a–C:H Thin Films by Spectroscopic Infrared Ellipsometry," A. Friedl et al., Review of Scientific Instruments, vol. 65, No. 9, Sep. 1994, pp. 2882–2889.

"Ellipsometric data processing: an efficient method and an analysis of the relative errors", by Charlot et al., Applied Optics/vol. 24, No. 20, Oct. 15, 1985, pp. 3368–3373.

"High–speed spectral ellipsometry for in situ diagnostics and process control", by W.M. Duncan et al., J. Vac. Sci. Technol. B, 12(4), Jul./Aug. 1994, pp. 2779–2784.

"Phase Modulated Ellipsometry From The Ultraviolet To The Infrared: In Situ Application To The Growth Of Semiconductors", by Drevillon, Prog. Crystal Growth & Charact. 1993, vol. 27, (no month).

*Primary Examiner*—Richard A. Rosenberger
*Attorney, Agent, or Firm*—Reid & Priest LLP

[57] ABSTRACT

This invention relates to a method and a device for the ellipsometric measurement of physical parameters representative of a sample.

The measured values $I_{om}$, $I_{sm}$ and $I_{cm}$ are calculated (51, 52) from the signal (50) which represents the measured intensity $I(t)$.

In a first step (55, 57), initial theoretical values $I_s/I_{ot}$ and $I_c/I_{ot}$ are produced from initial estimations (56) of the physical parameters. In a second step (58, 59) subsequent estimations (59) of physical parameters are determined from which subsequent theoretical values $I_s/I_{ot}$ and $I_c/I_{ot}$ are deduced (55, 57). The second step is reiterated to an Nth estimation (59) of the physical parameters, so as to minimise the difference between the theoretical values and those measured.

The physical parameters are evaluated (54) in the course of the Nth estimation.

10 Claims, 2 Drawing Sheets

METHOD OF ELLIPSOMETRIC MEASUREMENT, AN ELLIPSOMETER AND DEVICE FOR CONTROLLING THE CARRYING OUT OF LAYERS USING SUCH METHOD AND APPARATUS

FIELD OF THE INVENTION

This invention relates to a method and an apparatus for rapid ellipsometry, as well as a device for controlling the carrying out of layers using such method and apparatus.

BACKGROUND OF THE INVENTION

Ellipsometry is a technique of non-destructive measurement allowing optical characterisation of a sample having a specular or quasi-specular surface.

Ellipsometry can be implemented in situ and allows then the study of the mechanisms of thin layer growth, the formation of interfaces and the control of the carrying out method of said layers and interfaces. Ellipsometry is, for example, used for the study and the control of the manufacture of semi-conductors.

The ellipsometric measurements can be made at one fixed wavelength or at several wavelengths (spectroscopic ellipsometry). According to the wavelength region of the source, near ultra violet, visible, near infra red, infra red, etc., it is possible to have access to different properties of the layers, of the materials or to explore different materials.

In the ultra violet and visible regions, the depth of penetration of the radiation is often slight. This constitutes favourable conditions for the study of surfaces and interfaces, and for real time controls. Generally this does not allow access to layer volumic properties and materials which can, on the other hand, be obtained through measurements in the infra red region.

Infra red is well suited to measurements of vibrational absorption (chemical bonds).

In order to carry out ellipsometric measurements, the surface of a sample is illuminated by a light beam and the state of polarisation of an incident beam i is compared with that of the reflected beam r or the transmitted beam. A polarisation vector E is generally represented by its projections $E_S$ and $E_P$ respectively perpendicular and parallel to the plane of incidence. The projections $E_S$ and $E_P$ are complex amplitudes.

In the domain of ellipsometry, the relationship $p=(E_P/E_S)^r/(E_P/E_S)^i$, indicative of the modifications of the state of polarisation produced by the surface being studied, is generally represented in the form:

$$p = tg\Psi \cdot exp(i\Delta) = (E_P/E_S)^r/(E_P/E_S)^i$$

The two angles $\Psi$ and $\Delta$ describing the change in polarisation are thus combined in the complex quantity p.

The angles $\Psi$ and $\Delta$, and hence the number p, depend, at the same time, on the properties of the sample, the angle of incidence of a beam and the measurement wavelength. The expression of $\Psi$ and $\Delta$, or of p, as a function of these parameters, is given by the equations of Fresnel quoted, for example, by D. CHARLOT and A. MARUANI in Appl. Opt. 24, 3368, 1985.

In a phase modulation ellipsometer, an incident beam has its polarisation modulated by a phase difference generated between two appropriate axes by a phase modulator. The phase shift $\delta(t)$ develops typically with time t in accordance with a periodic pulse law $\omega$, $\delta(t)$ being proportional to the first order to $\sin(\omega t)$.

In a phase modulation ellipsometer, the intensity of a luminous flux reflected by a sample allows, in a known way, the values of $\Psi$ and $\Delta$ to be deduced.

Ellipsometry, and more particularly Spectroscopic Phase Modulated Ellipsometry (SPME) is a high performance technique for the measurement, in real time, of the growth of layers on a substrate. This technique has the advantage of not disturbing reactions in progress. Furthermore, it is very sensitive to the physical parameters of the measured sample, such as a thickness d of layer and an index of refraction n. Furthermore it enables measurements to be made rapidly.

In accordance with a known method, the angles $\Psi$ and $\Delta$ or p are deduced from intensity measurements. These quantities $\Psi$ and $\Delta$ depend on the physical parameters of the measured sample such as the refractive index n and the thickness d of the upper layer. These parameters can therefore be calculated subsequently from $\Psi$ and $\Delta$ by direct inversion of the Fresnel equations. This inversion must generally be carried out in an iterative manner.

The application of Spectroscopic Phase Modulated Ellipsometry, in situ, for diagnosis and for growth control, is, for example, described in the document "High Speed Spectral Ellipsometry for In Situ Diagnostics and Process Control_, DUNCAN et al., J. Vac. Sci. Technol. B., 12(4), 1984.

Despite its effectiveness, this method has the disadvantage, in certain circumstances, of generating uncertainties in the measurements of physical parameters. These uncertainties can arise, in particular, during growth of transparent material on an absorbent substrate. The accuracy of the measurements is thus substantially deteriorated.

SUMMARY OF THE INVENTION

The object of this invention is to put phase modulation ellipsometry into practice whilst freeing it from the problems of periodic oscillations and hence to improve the accuracy of the measurements.

Another object of the invention is to control the deposition of transparent material onto a substrate without any special difficulty.

It is also an object of the invention to measure physical parameters during the deposition of a film onto a substrate at increased speed, for example greater than 30 Å·s$^{-1}$ up to a considerable thickness, for example, greater than 4000 Å, with good accuracy.

An additional object of the invention is to measure physical parameters of a sample such as n and d, without having to measure the angles $\Psi$ and $\Delta$, or the number p.

To this end, the invention relates to a method for the ellipsometric measurement of physical parameters, representative of a sample. In this method:

- an incident light beam is linearly polarised, said beam being defined by a polarisation vector,
- the incident light beam of polarised light is modulated in such a way that a phase shift $\delta(t)$ is brought about between the perpendicular components of the polarisation vector, depending on the time t according to a periodic pulse variation $\omega$, $\delta(t)$ being proportional to the first order to $\sin(\omega t)$,
- the sample is illuminated with the incident light beam of modulated polarised light,
- the polarisation vector of the light incident reflected by the sample is analysed,
- a flux of the light beam is measured by means of at least one photodetector, calculations are carried out on the flux measurements by an electronic processing unit connected to the photodetector.

The detected flux having an intensity I(t) of the form:

$$I(t) = I_{om} + I_{sm} \sin \delta(t) + I_{cm} \cos \delta(t)$$

$I_{om}$, $I_{sm}$ and $I_{cm}$ being the values measured in the processing unit from the intensity I(t) and depending on said physical parameters.

According to the invention:

in a first step, initial theoretical values $I_s/I_{ot}$ and $I_c/I_{ot}$ are produced from initial estimations of the physical parameters, said theoretical values are used to determine, in a second step, subsequent estimations of physical parameters from which the subsequent theoretical values $I_s/I_{ot}$ and $I_c/I_{ot}$ are deduced, the second step being reiterated until the Nth estimation of the physical parameters so as to minimise the difference between the theoretical values and those measured.

The physical parameters being evaluated from the values of $I_s/I_{ot}$ and $I_c/I_{ot}$ found in the course of the Nth estimation.

In contrast to known methods, the method according to the invention does not require knowledge of Ψ and Δ. The determination of the physical parameters is carried out directly from the measured values $I_{om}$, $I_{sm}$ and $I_{cm}$ obtained from the intensity I(t). Instead of inverting the Fresnel equations, the equations giving the preceding values are adjusted as a function of the physical parameters, the method in this case also being iterative.

Instead of working with one single point, an averaging or an integration is carried out over a group of points to make the adjustments. Typically, several tens of points are processed at a time. These points are obtained for a series of measurements at successive points in time or at several wavelengths. Obtaining the points at successive points in time is used preferably for kinetic measurements and obtaining points at different wavelengths for static measurements.

In a case where there is deposition of several successive layers on one substrate, an update is carried out on the averaged series of points when changing to a new layer.

This technique allows avoiding the use of troublesome values of Ψ and Δ which would cause measurement inaccuracies.

This happens particularly when Ψ is close to 45°.

Furthermore, during the deposition of a transparent material onto an absorbent substrate, an incident beam is subjected to multiple interference within the transparent layer. A layer, even a relatively thick one, does not avoid this interference so that it does not reduce the influence of the substrate in relation to that of the layer, on the reflection properties. The result is that Ψ and Δ do not converge towards an arrival point corresponding to the optical properties of the layer as is the case for the deposition of an absorbent material. On the contrary, Ψ and Δ are subject to considerable, periodic variations in the course of the growth.

Thus, methods based on the inversion of Fresnel equations diverge when used for thicknesses of a layer of refractive index n such as $$d = \frac{k\lambda}{2\sqrt{(n^2 - \sin^2\Phi_o)}}$$

where k is an integer, $\Phi_o$ being the angle of incidence of an incident beam and λ the measuring wavelength.

The significant variations in Ψ and Δ during the deposition of a transparent material do not allow avoiding the zones of instability bringing about the inaccuracies mentioned above. By freeing the calculations from Ψ and Δ and using an average, it is possible to reduce these disadvantages considerably.

Moreover, one step is gained in the acquisition of data since Ψ and Δ are deduced from $I_{om}$, $I_{sm}$ and $I_{cm}$ in the known methods.

A stop test, known per se, is necessary to stop the iterations. It consists typically of comparing the theoretical values $I_s/I_{ot}$ and $I_c/I_{ot}$ with the measured values $I_{sm}/I_{om}$ and $I_{cm}/I_{om}$. When the difference becomes less than a fixed percentage error, the iterations are stopped.

Moreover, the initial estimations of physical parameters do not require any great precision, the iteration causing them to converge rapidly. In a known way, it is advantageous to choose previously calculated physical parameters as initial estimations.

A few iterations are sufficient for the physical parameters to converge. Their evaluation is therefore very rapid and can be carried out with a standard microcomputer. The determination of the thickness d and the refractive index n of a layer deposited on a substrate is carried out typically in about two seconds with an accuracy of the order of 1% on the product n×d, with a microcomputer such as those known under the name _PC 486_.

According to a preferred embodiment of the method of measurement according to the invention, first calculation means of the processing unit give Fourier components $S_0$, $S_1$ and $S_2$ of said flux intensity respectively, continuous, at the pulse ω and at the pulse 2ω. Second calculation means allow the measured values $I_{om}$, $I_{sm}$ and $I_{cm}$ to be deduced linearly from the components $S_0$, $S_1$ and $S_2$. A description of these steps by B. DREVILLON will be found in "Progress in Crystal Growth and Characterisation of Materials", vol. 27, pp. 1-87, 1993.

According to a preferred embodiment of the invention, the sample comprises at least one transparent layer illuminated by an incident beam.

In effect, the method according to the invention is then particularly advantageous in relation to known methods as has already been seen. The transparent material is, for example, silica, the substrate possibly being made of silicon.

The method according to the invention is also applicable to absorbent materials.

According to a preferred embodiment of the invention, the difference between theoretical values and measured values is minimised by a method of least squares.

This choice of least squares gives the difference between the theoretical and measured values. A conventional method such as the Levenberg-Marquardt method is used to minimise this difference.

According to a particularly advantageous embodiment of the method of measurement, the method of measurement is spectroscopic.

It is thereby possible to vary the measurement wavelength. Typically, a broad spectrum light source emits an incident beam, this is reflected by the sample, then a wavelength of the reflected beam is selected by use of a monochromator. Another way of choosing a given wavelength consists of varying the wavelength of the source.

In sequential spectroscopic apparatus, one wavelength is selected successively after the other. Instead of these traditional devices, one can also use spectroscopic apparatus of the multiplex type. Dispersed beams are detected on several photodetectors and electronic multiplexing is carried out on the signals picked up. This multiplex type of spectroscopic apparatus allows simultaneous measurements with several wavelengths.

The invention also relates to an ellipsometer comprising a light source emitting a light incident beam, a polariser linearly polarising the light beam, a phase modulator generating a phase shift $\delta(t)$ dependent to the first order on time t in accordance with a periodic pulse variation $\omega$, $\delta(t)$ being proportional to the first order to $\sin(\omega t)$, an analyser analysing the state of polarisation of the light beam reflected by a sample illuminated by the incident light beam of polarised light, a photodetector measuring a light beam flux, and an electronic processing unit connected to the photodetector carrying out calculations on the flux measurements.

The detected flux has an intensity I(t) of the form:

$$I(t) = I_{om} + I_{sm} \sin \delta(t) + I_{cm} \cos \delta(t)$$

$I_{om}$, $I_{sm}$ and $I_{cm}$ being the values measured in the processing unit from the intensity I(t) and depending on said physical parameters.

In the ellipsometer according to the invention:

the processing unit produces initial theoretical values $I_{st}/I_{ot}$ and $I_{ct}/I_{ot}$ from initial estimations of the physical parameters, said theoretical values being used to determine subsequent estimations of physical parameters from which the subsequent theoretical values $I_{st}/I_{ot}$ and $I_{ct}/I_{ot}$ are deduced, this operation being reiterated until the Nth estimation of the physical parameters, so as to minimise the difference between the theoretical values and those measured.

The physical parameters being evaluated from the values of $I_{st}/I_{ot}$ and $I_{ct}/I_{ot}$ found in the course of the Nth estimation.

In a preferred embodiment of the ellipsometer, according to the invention, it comprises at least one fibre from the group formed by a first and a second optical fibre, the first optical fibre being placed between the source and the polariser and the second optical fibre being placed between the analyser and a detection system which includes the photodetector.

In addition to the photodetector, the detection system is liable to comprise a monochromator for ellipsometric measurements at one wavelength or a spectrograph for simultaneous measurements at several wavelengths. In the case of an emission of a laser beam, the detection system may only contain the photodetector.

The invention also relates to a device for controlling the carrying out of layers on a substrate comprising means for controlling physical parameters representative of the carrying out of layers.

The substrate and the layers constituting a sample, the control means comprise:

a light source emitting a light incident beam, a polariser linearly polarising the light beam, a phase modulator generating a phase shift $\delta(t)$ dependent to the first order on time t in accordance with a periodic pulse variation $\omega$, $\delta(t)$ being proportional, to the first order, to $\sin(\omega t)$, an analyser analysing the state of polarisation of the light beam reflected by the sample illuminated by the incident light beam of polarised light, at least one photodetector measuring a light beam flux, and an electronic processing unit connected to the photodetector carrying out calculations on the flux measurements.

The detected flux has an intensity I(t) of the form:

$$I(t) = I_{om} + I_{sm} \sin \delta(t) + I_{cm} \cos \delta(t)$$

$I_{om}$, $I_{sm}$ and $I_{cm}$ being the values measured in the processing unit from the intensity I(t) and depending on the physical parameters.

In the control device according to the invention:

the processing unit produces initial theoretical values $I_{st}/I_{ot}$ and $I_{ct}/I_{ot}$ from initial estimations of the physical parameters, said theoretical values being used to determine subsequent estimations of physical parameters from which the subsequent theoretical values $I_{st}/I_{ot}$ and $I_{ct}/I_{ot}$ are deduced, this operation being reiterated until the Nth estimation of the physical parameters, so as to minimise the difference between the theoretical values and those measured.

The physical parameters being evaluated from the values $I_{st}/I_{ot}$ and $I_{ct}/I_{ot}$ found in the course of the Nth estimation.

The carrying out of layers can be a deposition onto a substrate.

This device is thus particularly well suited to the control of the deposition of layers carried out by techniques such as MOCVD (Metalorganic Chemical Vapour Deposition), PECVD (Plasma Enhanced Chemical Vapour Deposition) or MBE (Molecular Beam Epitaxy).

The carrying out of layers can also be made by etching.

Measurements according to the invention allow, not only the mechanism of growth to be observed but also enable a method of control incorporating feedback to be carried out in real time. It is therefore possible to act, in real time, on the parameters involved in the carrying out of layers.

Accurate measurements are thus made without disturbing the growth mechanisms.

In the device for controlling the carrying out of layers, the layers each having a thickness, a refractive index and a dielectric function, the physical parameters preferably include at least certain of them.

In the control device according to the invention, the carrying out being a deposition, the rate of deposition of a layer is greater than 30 Ås$^{-1}$.

For such a rate, measurements obtained with the device according to the invention are particularly accurate compared to measurements made with a known device, with the same capacity for calculation.

BRIEF DESCRIPTION OF THE DRAWINGS

One embodiment of the invention will be described in detail, with reference to the appended drawings, in which.

DETAILED DESCRIPTION OF THE PREFERRED EMBODIMENT

Figure 1:
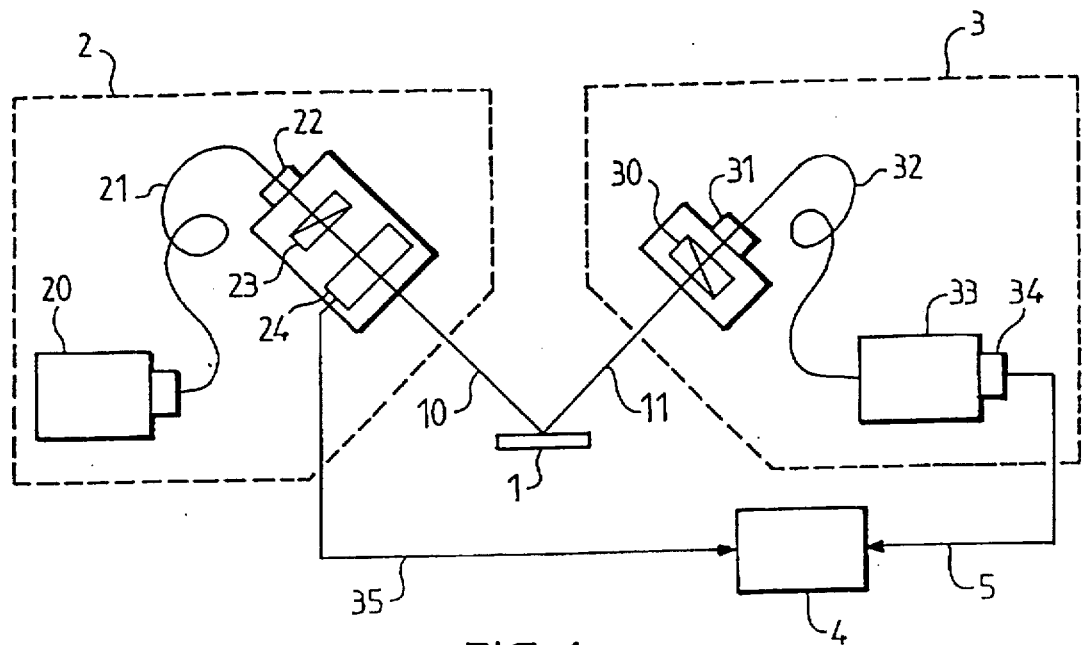
FIG. 1 is a schematic representation of an apparatus for ellipsometric measurement at one wavelength, according to the invention.

The single wavelength ellipsometer, shown in FIG. 1 is intended to measure the physical parameters of a sample 1. It comprises an excitation assembly 2, an analysis assembly 3 and an electronic processing unit 4.

The excitation assembly 2 comprises a light source 20 linked to an optical system 22 by means of an optical fibre 21, the optical system 22 directing a light beam emitted by the source 20 towards the sample 1. The excitation assembly 2 also comprises a polariser 23 followed by a phase modulator 24 between the optical system 22 and the sample 1. It brings about a phase shift $\delta(t)$.

The analysis assembly 3 comprises an analyser 30 which analyses a beam reflected by the sample 1, followed by an optical system 31 which sends the reflected beam to a monochromator 33 through an optical fibre 32. The monochromator 33 is linked to a photodetector 34 which converts the detected flux intensity into an electrical signal. This signal is represented by $I(t)$.

This signal is supplied to the electronic processing unit 4 by means of a connection 5. The electronic processing unit 4 also receives a frequency reference and a phase reference from the phase modulator 24 via a line 35.

When in operation, the light source 20 emits an incident light beam 10 having a given wavelength range, this beam being polarised by the polariser 23, then subjected to modulation by phase modulator 24. The phase modulator 24 typically consists of a bar of fused silica subjected to a periodic stress generated by a piezoelectric transducer. A phase shift $\delta(t)$ is thereby created, modulated with time t between two suitable axes of this bar. The polarisation of the light emergent beams is thus modulated.

The polarised and modulated, incident light beam 10 becomes, after reflection from sample 1, a reflected beam 11, having an amplitude and a phase that is a consequence of the physical properties of the sample 1. This reflected beam 11 is analysed in the analyser 30, then a wavelength $\lambda$ is selected by the monochromator 33. A flux of the light beam 11 is measured by the photodetector 34 which supplies an electric signal, generated by the flux intensity, to the processing unit 4.

Figure 2:
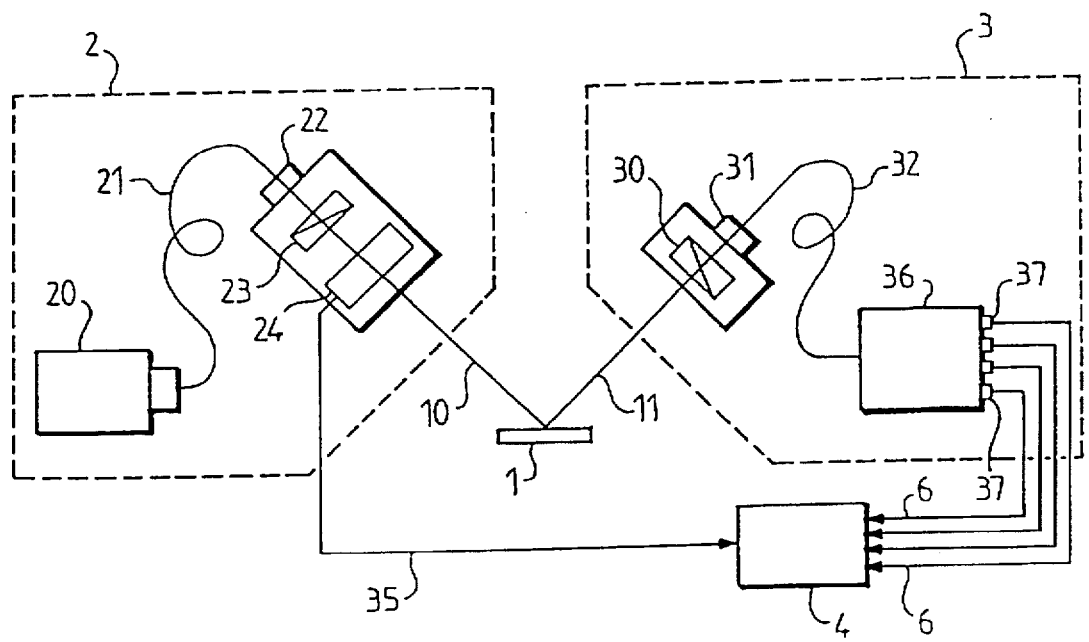
FIG. 2 is a schematic representation of an apparatus for ellipsometric measurement at several wavelengths, according to the invention.

The multiple wavelength ellipsometer shown in FIG. 2 differs from the single wavelength ellipsometer in FIG. 1 in the analysis assembly 3 and the connections between the latter and the electronic processing unit 4.

Instead of monochromator 33 and photodetector 34, the analysis assembly 3 comprises a spectrograph 36 and a series of photodetectors 37. Each of the photodetectors 37 allows the measurement of one wavelength and is linked to the unit 4 by a connection 6.

Hence, the multiple wavelength ellipsometer in FIG. 2 allows the simultaneous measurement of several wavelengths, multiplexing being possible in unit 4.

Figure 3:
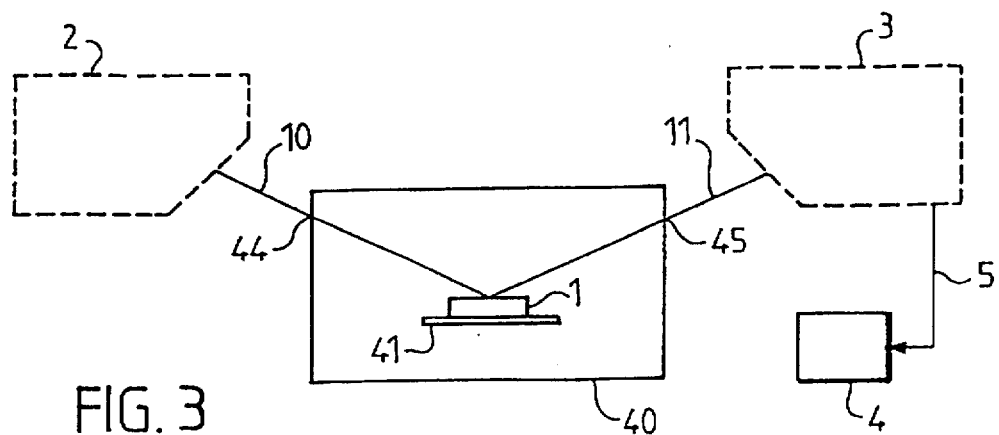
FIG. 3 is a schematic representation of a device for controlling the carrying out of layers on a substrate according to the invention.

The spectroscopic phase modulated ellipsometer, shown in FIGS. 1 or 2, is advantageously used in a device for controlling the carrying out of layers on a substrate, shown in FIG. 3. Sample 1 consists of a substrate on which a deposit will be grown using a known technique. Sample 1 is positioned on a stage 41 and contained in a chamber 40. The ellipsometric measuring apparatus previously described is used to control the growth of layers on the substrate. Windows 44 and 45 are opened up along the optical paths leading respectively from the excitation assembly 2 to the chamber 40, and from the chamber 40 to the analysis assembly 3.

A light incident beam 10 is thus carried directly to chamber 40, then the beam 11, reflected by sample 1, is transmitted to the analysis assembly 3.

By this means, in situ measurements are carried out which do not disturb the growth process.

Instead of growth of layers, the carrying out can consist of an etching.

Figure 4:
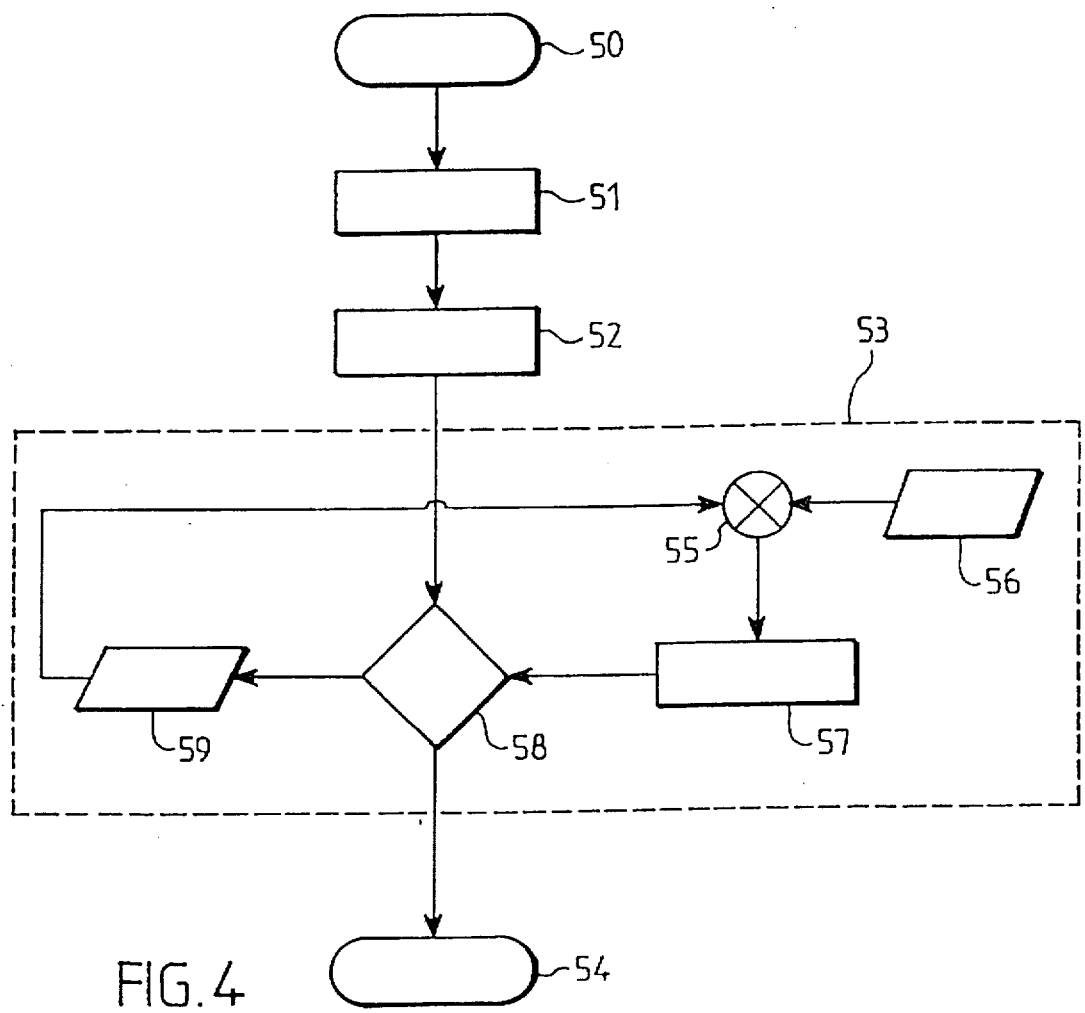
FIG. 4 is a flowchart for the ellipsometric method for measuring physical parameters according to the invention.

The signal received by the processing unit 4, after detection of the reflected beam 11, is then subjected to the following operations which are shown schematically in FIG. 4.

First, from a signal 50, representative of a measured intensity $I(t)$, measured values $I_{om}$, $I_{sm}$ and $I_{cm}$ are extracted by a method known per se. $I_{om}$, $I_{sm}$ and $I_{cm}$, known under the name of Mueller matrix coefficients in the case of a specular reflection, are linked to $I(t)$ by the equation $$I(t) = I_{om} + I_{sm} \sin \delta(t) + I_{cm} \cos \delta(t)$$

In a first step 51, the Fourier components $S_0$, $S_1$ and $S_2$ of the intensity $I(t)$ respectively, continuous, at the modulation pulse $\omega$ and at the pulse $2\omega$, are calculated. These components are extracted in a classic way, for example by a discrete Fourier transform.

In a step 52, the measured values $I_{om}$, $I_{sm}$ and $I_{cm}$ are deduced from the components $S_0$, $S_1$ and $S_2$ by known linear equations.

According to the invention, it is not necessary to know $\Psi$ and $\Delta$, or p. An iterative method 53 is applied directly to the measured values $I_{om}$, $I_{sm}$ and $I_{cm}$ which leads to an evaluation 54 of physical parameters representative of sample 1.

Typically, these physical parameters consist of the thickness d of a film deposited on a substrate, its refractive index n and its dielectric function.

According to the iterative method 53, initial estimations 56 of the physical parameters are used as input parameters 55.

Initial theoretical values $I_s/I_{ot}$ and $I_c/I_{ot}$ are deduced from them in accordance with known formulae. The theoretical values $I_s/I_{ot}$ and $I_c/I_{ot}$ are, in fact, expressed as combinations of trigonometric functions of $\Psi$ and $\Delta$. In addition, the angles $\Psi$ and $\Delta$ are linked to the physical parameters being sought with the Fresnel equations. The theoretical values $I_s/I_{ot}$ and $I_c/I_{ot}$ can therefore be directly expressed as a function of the physical parameters.

The theoretical values obtained in step 57 are compared with the measured values $I_{sm}/I_{om}$ and $I_{cm}/I_{om}$ determined in step 52. This comparison 58 requires that the difference between the theoretical and the measured values be quantified. To do this, a method of least squares, known per se, is used. On the other hand, an averaging of a series of M points is carried out. Indexing the measurement points by j, the square of the difference between theoretical and measured values is obtained classically as:

$$\sum_{j=1}^{M} [(I_{sm}/I_{om})_j - (I_s/I_{ot})_j]^2 + [(I_{cm}/I_{om})_j - (I_c/I_{ot})_j]^2$$

An adjustment method other than the method of least squares can be used, such as the maximum likelihood method or the replacement of squares by other powers.

The calculated difference is compared with a predetermined threshold which is function of the accuracy desired. If the difference is less than the threshold, the approximation of the measured values is satisfactory and the physical parameters used to calculate them give the evaluation 54. In the contrary case, the error is too large and a new iteration is necessary. The comparison 58 then leads to specification of subsequent estimations 59 of the physical parameters. The determination of these subsequent estimations is a matter of using known methods to minimise the difference, such as the Levenberg-Marquardt method.

These subsequent estimations 59 are themselves used as input 55 of parameters calculate the subsequent theoretical values $I_s/I_{ot}$ and $I_c/I_{ot}$ reiterating step 57. These subsequent theoretical values themselves serve as a basis for the comparison 58 with the measured values $I_{sm}/I_{om}$ and $I_{cm}/I_{om}$ All of these steps, making up the loop 59, 55, 57, 58 are repeated until the difference obtained when making comparison 58 is less than the predetermined threshold. From the Nth estimation of the physical parameters associated with these theoretical values, the evaluation 54 of the physical parameters is deduced.

This method of ellipsometric measurement according to the invention avoids problems posed by the known method based on the direct inversion of the equations of Fresnel such as for thicknesses $$d = \frac{k\lambda}{2\sqrt{(n^2 - \sin^2\Phi_o)}}$$

and for $\Psi$ close to 45°.

Moreover, this method according to the invention does not require that $\Psi$ and $\Delta$ be calculated, but allows the physical parameters which are being sought to be obtained more directly.

Generally, three or four iterations are sufficient to obtain the parameters, for each measurement. The use of a "PC 486" micro-computer enables the thickness d and the refractive index n of a layer deposited on a substrate to be determined in less than two seconds. Typically, the method according to the invention allows measurements with an accuracy of 3% up to a layer thickness of 5 to 6000 Å, for a high deposition rate of the order of 30 Å·s$^{-1}$.

The accuracy of measurement decreases with the thickness of the layer deposited. Moreover, the method according to the invention allows obtaining a very high accuracy for the product n×d. This accuracy is of the order of 1% for the case referred to previously.

The method according to the invention allows control of the homogeneity of a layer deposited on a substrate as regards thickness and composition. It is suitable for the deposition of an absorbent material as for a transparent material. It also allows control of the carrying out of multilayer systems including stacking.

We claim:

1. A method for the ellipsometric measurement of physical parameters representative of a sample in which:

an incident light beam is linearly polarised, said beam being defined by a polarisation vector, the light incident beam of polarised light is modulated in such a way that a phase shift $\delta(t)$ is brought about between the perpendicular components of the polarisation vector, depending on the time t according to a periodic pulse variation $\omega$, $\delta(t)$ being proportional to the first order to $\sin(\omega t)$, the sample is illuminated with the light incident beam of modulated polarised light, the polarisation vector of the light beam reflected by the sample is analysed, a flux of the light beam is measured by means of at least one photodetector, calculations are carried out on the flux measurements by an electronic processing unit connected to the photodetector the detected flux having an intensity I(t) of the form:

$$I(t) = I_{om} + I_{sm} \sin \delta(t) + I_{cm} \cos \delta(t)$$

$I_{om}$, $I_{sm}$ and $I_{cm}$ being the values measured in the processing unit from the intensity I(t), and depending on said physical parameters, wherein:

in a first step, initial theoretical values $I_s/I_{ot}$ and $I_c/I_{ot}$ are produced from initial estimations of the physical parameters, said theoretical values are used to determine, in a second step, subsequent estimations of physical parameters from which the subsequent theoretical values $I_s/I_{ot}$ and $I_c/I_{ot}$ are deduced, the second step being reiterated until the Nth estimation of the physical parameters, so as to minimise the difference between the theoretical values and those measured, the physical parameters being evaluated from the values of $I_s/I_{ot}$ and $I_c/I_{ot}$ found in the course of the Nth estimation.

2. A measurement method according to claim 1, wherein:

first calculation means of the processing unit give Fourier components $S_0$, $S_1$ and $S_2$ of said flux intensity, respectively, continuous, at the pulse $\omega$ and at the pulse $2\omega$, second calculation means allow deduction linearly of components $S_0$, $S_1$ and $S_2$ from measured values $I_{om}$, $I_{sm}$ and $I_{cm}$.

3. A method according to claim 1, wherein the sample comprises at least one transparent layer illuminated by an incident beam.

4. A method according to claim 1, wherein said difference between theoretical and measured values is minimised by a method of least squares.

5. A method according to any 1, wherein the method of measurement is spectroscopic.

6. An ellipsometer comprising:

a light source emitting a light incident beam, a polariser linearly polarising the light beam, a phase modulator generating a phase shift d(t) dependent to the first order on time t in accordance with a periodic pulse variation $\omega$, d(t) being proportional to the first order to $\sin(\omega t)$, an analyser analysing the state of polarisation of the light beam reflected by a sample illuminated by the incident light beam of polarised light, at least one photodetector measuring a light beam flux, and an electronic processing unit connected to the photodetector, carrying out calculations on the flux measurements, the detected flux having an intensity I(t) of the form:

$$I(t) = I_{om} + I_{sm} \sin \delta(t) + I_{cm} \cos \delta(t)$$

$I_{om}$, $I_{sm}$ and $I_{cm}$ being the values measured in the processing unit from the intensity I(t), and depending on said physical parameters, wherein:

the processing unit produces initial theoretical values $I_s/I_{ot}$ and $I_c/I_{ot}$ from initial estimations of the physical parameters, said theoretical values being used to determine subsequent estimations of physical parameters from which the subsequent theoretical values $I_s/I_{ot}$ and $I_c/I_{ot}$ are deduced, this operation being reiterated until the Nth estimation of the physical parameters, so as to minimise the difference between the theoretical values and those measured, the physical parameters being evaluated from the values of $I_s/I_{ot}$ and $I_c/I_{ot}$ found in the course of the Nth estimation.

7. An ellipsometer according to claim 6, wherein it comprises at least one fibre from the group formed by a first and a second optical fibre, the first optical fibre being placed between the source and the polariser and the second optical fibre being placed between the analyser and a detection system which includes the photodetector.

8. A device for controlling the carrying out of layers comprising means for controlling physical parameters representative of the carrying out of layers, the substrate and the layers constituting a sample, said control means comprising:

a light source emitting a light incident beam, a polariser linearly polarising the light beam, a phase modulator generating a phase shift d(t) dependent to the first order on time t in accordance with a periodic pulse variation ω, d(t) being proportional to the first order to sin(ωt), an analyser analysing the state of polarisation of the light beam reflected by the sample illuminated by the incident light beam of polarised light, at least one photodetector measuring a light beam flux, and an electronic processing unit connected to the photodetector, carrying out calculations on the flux measurements, the detected flux having an intensity I(t) of the form:

$$I(t) = I_{om} + I_{sm} \sin d(t) + I_{cm} \cos d(t)$$

$I_{om}$, $I_{sm}$ and $I_{cm}$ being the values measured in the processing unit from the intensity I(t), and depending on said physical parameters, wherein:

the processing unit produces initial theoretical values $I_s/I_{ot}$ and $I_c/I_{ot}$ from initial estimations of the physical parameters, said theoretical values being used to determine subsequent estimations of physical parameters from which the subsequent theoretical values $I_s/I_{ot}$ and $I_c/I_{ot}$ are deduced, this operation being reiterated until the Nth estimation of the physical parameters, so as to minimise the difference between the theoretical values and those measured, the physical parameters being evaluated from the values of $I_s/I_{ot}$ and $I_c/I_{ot}$ found in the course of the Nth estimation.

9. A device according to claim 8, wherein, the layers each have a thickness, a refractive index and a dielectric function, the physical parameters including at least certain of them.

10. A device according to claim 8, wherein, the carrying out being a deposition, the rate of deposition of a layer is greater than 30 $\text{Ås}^{-1}$.

* * * * *